(12) United States Patent
Avagliano et al.

(10) Patent No.: US 9,192,902 B2
(45) Date of Patent: Nov. 24, 2015

(54) UREA REACTOR TRAY, REACTOR, AND PRODUCTION PROCESS

(75) Inventors: Ugo Avagliano, San Donato Milanese (IT); Lino Carlessi, Dalmine (IT)

(73) Assignee: SAIPEM S.p.A., San Donato Milanese (IT)

(\*) Notice: Subject to any disclaimer, the term of this patent is extended or adjusted under 35 U.S.C. 154(b) by 0 days.

(21) Appl. No.: 14/232,137

(22) PCT Filed: Jul. 4, 2012

(86) PCT No.: PCT/IB2012/053421
§ 371 (c)(1),
(2), (4) Date: Mar. 6, 2014

(87) PCT Pub. No.: WO2013/008147
PCT Pub. Date: Jan. 17, 2013

(65) Prior Publication Data
US 2014/0171686 A1    Jun. 19, 2014

(30) Foreign Application Priority Data
Jul. 12, 2011    (IT) .............................. MI2011A1299

(51) Int. Cl.
*B01J 10/00* (2006.01)
*C07C 273/04* (2006.01)
*B01J 8/06* (2006.01)
*B01F 3/04* (2006.01)
(Continued)

(52) U.S. Cl.
CPC . *B01J 8/06* (2013.01); *B01D 3/009* (2013.01); *B01D 3/22* (2013.01); *B01F 3/04* (2013.01); *B01J 10/00* (2013.01); *B01J 19/0053* (2013.01); *C07C 273/04* (2013.01)

(58) Field of Classification Search
USPC ..................................... 564/67; 422/606, 607
See application file for complete search history.

(56) References Cited

U.S. PATENT DOCUMENTS 2,006,986 A * 7/1935 De Florez Luis .......... 261/114.1
3,018,094 A * 1/1962 Mikkelson .................... 261/113
(Continued)

FOREIGN PATENT DOCUMENTS

CN         1154664 A      7/1997
EP         0 055 496      7/1982
(Continued)

OTHER PUBLICATIONS

Chinese Office Action for Chinese Patent Application No. 2012800347552 dated Sep. 28, 2014 (25 Pages).
(Continued)

*Primary Examiner* — Jennifer A Leung
(74) *Attorney, Agent, or Firm* — Neal, Gerber & Eisenberg LLP (57) ABSTRACT

A urea reactor tray having a base plate; and a number or quantity of hollow cup-shaped members, which project vertically from the base plate along respective substantially parallel axes perpendicular to the base plate, and have respective substantially concave inner cavities communicating with respective openings formed in the base plate; the tray having a number or quantity of first cup-shaped members, each of which extends axially between an open top end having the opening, and a closed bottom end, and has a lateral wall with through holes substantially crosswise to the axis, and a bottom wall which closes the closed bottom end and has no holes.

28 Claims, 3 Drawing Sheets

(51) Int. Cl.
  *B01D 3/00* (2006.01)
  *B01D 3/22* (2006.01)
  *B01J 19/00* (2006.01)

(56) References Cited

U.S. PATENT DOCUMENTS

| | | | |
|---|---|---|---|
| 3,070,359 A * | 12/1962 | Canevari | 261/113 |
| 3,070,360 A | 12/1962 | Rafferty et al. | |
| 3,222,040 A | 12/1965 | Eckert | |
| 3,779,527 A * | 12/1973 | Tanigawa et al. | 261/114.1 |
| 3,922,326 A | 11/1975 | Yoshida et al. | |
| 5,304,353 A | 4/1994 | Dente et al. | |
| 5,593,548 A | 1/1997 | Yeoman et al. | |
| 6,165,315 A | 12/2000 | Jonckers et al. | |
| 6,444,180 B1 | 9/2002 | Zardi et al. | |
| 2009/0200690 A1 | 8/2009 | Maleta et al. | |

FOREIGN PATENT DOCUMENTS

| | | |
|---|---|---|
| EP | 0 495 418 | 7/1992 |
| EP | 0 694 325 | 1/1996 |
| EP | 0 781 164 | 7/1997 |
| GB | 1 294 926 | 11/1972 |

OTHER PUBLICATIONS

International Search Report and Written Opinion for International Application No. PCT/IB2012/053421 dated Feb. 12, 2013.
Notification Concerning Submission, Obtention or Transmittal of Priority Document (Form PCT/IB/304) for International Application No. PCT/IB2012/053421 dated Aug. 9, 2012.
Response to International Search Report and the associated Written Opinion for International Application No. PCT/IB2012/053421 dated May 9, 2013.
PCT Demand (Form PCT/IPEA/401) for International Application No. PCT/IB2012/053421.
Notification of Receipt of Demand by Competent International Preliminary Examining Authority (Form PCT/IPEA/402) for International Application No. PCT/IB2012/053421 dated Jun. 5, 2013.
Notification of Transmittal of the International Preliminary Report on Patentability (Form PCT/IPEA/416) for International Application No. PCT/IB2012/053421 dated Jul. 5, 2013.
International Preliminary Report on Patentability (Form PCT/IPEA/409) for International Application No. PCT/IB2012/053421 dated Jul. 5, 2013.

* cited by examiner

UREA REACTOR TRAY, REACTOR, AND PRODUCTION PROCESS

PRIORITY CLAIM

This application is a national stage application of PCT/IB2012/053421, filed on Jul. 4, 2012, which claims the benefit of and priority to Italian Patent Application No. MI2011A 001299, filed on Jul. 12, 2011, the entire contents of which are each incorporated by reference herein.

BACKGROUND

As is known, urea is produced industrially using processes whereby carbon dioxide reacts with ammonia to form ammonium carbamate, which decomposes into urea and water.

A typical reactor therefore contains a gaseous phase and a liquid phase flowing in co-current flows inside a pressurized reaction chamber.

Conversion of ammonia and carbon dioxide to ammonium carbonate and ultimately urea is enhanced (i.e., to increase urea output) using tray reactors.

Urea tray reactors substantially comprise a normally cylindrical shell, which extends substantially along a normally vertical axis, and is fitted inside with elements (i.e., trays) defined by respective metal sections shaped and/or perforated to divide the reaction chamber into compartments and form specific paths for the substances inside the reactor.

Certain known trays are perpendicular to the vertical axis of the reactor, and equally spaced along the axis to the full height of the reactor.

The trays are very often perforated (i.e., have holes variously arranged and possibly of different shapes and/or sizes).

In one embodiment, the trays are configured to be inserted through the manhole reactors are normally provided with, so they can also be fitted to existing reactors and/or removed and replaced. For which reason, the trays are normally made in a number or quantity of parts that fit together.

The trays have various functions, and in particular:
maximize the hold time of the light (faster) phase;
distribute the reactants as evenly as possible along the reactor section, to prevent 'back-mixing';
enhance mixing of the gaseous and liquid phases; and
reduce 'bubble size' to improve diffusion of the ammonia in the carbon dioxide.

Numerous urea reactor tray designs and configurations are known.

Urea reactors with perforated trays are described, for example, in European Patent No. 495418, European Patent No. 781164, U.S. Pat. No. 6,444,180 and U.S. Pat. No. 6,165,315.

Other tray designs for other applications are described in U.S. Pat. No. 3,070,360 and U.S. Pat. No. 3,222,040.

Certain known configurations—particularly those in certain of these patent documents specifically configured for producing urea—indeed provide for increasing output by reducing back-mixing and load losses, by ensuring substantially even distribution of the light (gaseous) and heavy (liquid) phases by providing preferential paths for each of the two phases, and by enabling non-intrusive (non-impact) mixing between one tray and another.

Certain known solutions, however, still leave room for improvement.

Generally speaking, certain known solutions fail to provide for thorough mixing of the light and heavy phases (both including supercritical fluids), which, because of the difference in density, tend to flow along separate preferential paths defined by the configuration and arrangement of the trays, and in particular by the shape, location, and size of the holes in the trays.

This drawback also impairs final conversion of the reactants, thus reducing urea output.

SUMMARY

The present disclosure relates to a urea reactor tray, reactor, and production process.

It is an advantage of the present disclosure to provide a urea reactor tray, reactor, and production process configured to eliminate certain of the above drawbacks of certain of the known art, and which, in particular, provide for thorough mixing of the gaseous and liquid phases, and high urea output.

One embodiment of the present disclosure therefore relates to a urea reactor tray comprising at least one base plate; and a quantity or number of hollow cup-shaped members, which project vertically from the base plate along respective substantially parallel axes perpendicular to the base plate, and have respective substantially concave inner cavities communicating with respective openings formed in the base plate; the tray comprising a quantity or number of first cup-shaped members, which project downwards from a bottom face of the base plate and each of which extends axially between an open top end having the opening, and a closed bottom end; each first cup-shaped member comprising a lateral wall with through circulation holes substantially crosswise to the axis and for preferential throughflow of a gaseous phase and/or liquid phase; and a bottom wall which closes the closed bottom end and has no circulation holes; the tray being characterized in that the lateral wall of each first cup-shaped member has first circulation holes predominantly for throughflow of a gaseous phase, and second circulation holes predominantly for throughflow of a liquid phase, all substantially crosswise to the axis; the first holes being located closer to the open top end than the second holes, and the first holes being smaller than the second holes.

Another embodiment of the present disclosure relates to a urea reactor comprising a shell extending substantially along a vertical axis (X) and defining a reaction chamber; and a quantity or number of reactor trays housed in a mutual spatial relationship inside the shell; the reactor being characterized in that the trays each comprise at least one base plate; and a quantity or number of hollow cup-shaped members, which project vertically from the base plate along respective substantially parallel axes perpendicular to the base plate, and have respective substantially concave inner cavities communicating with respective openings formed in the base plate; the tray comprising a quantity or number of first cup-shaped members, which project downwards from a bottom face of the base plate and each of which extends axially between an open top end having the opening, and a closed bottom end; each first cup-shaped member comprising a lateral wall with through circulation holes substantially crosswise to the axis and for preferential throughflow of a gaseous phase and/or liquid phase; and a bottom wall which closes the closed bottom end and has no circulation holes; the tray being characterized in that the lateral wall of each first cup-shaped member has first circulation holes predominantly for throughflow of a gaseous phase, and second circulation holes predominantly for throughflow of a liquid phase, all substantially crosswise to the axis; the first holes being located closer to the open top end than the second holes, and the first holes being smaller than the second holes.

Another embodiment of the present disclosure relates to a urea production process comprising the step of: producing a reaction between ammonia and carbon dioxide inside a reactor by feeding an ammonia-containing liquid phase and a carbon-dioxide-containing gaseous phase in the same upward direction inside the reactor and through compartments separated by trays; the gaseous phase and liquid phase flowing from one compartment to the next through transverse holes formed through lateral walls of a quantity or number of hollow first cup-shaped members projecting downwards from each tray along respective axes and between respective open top ends and respective closed bottom ends; said first cup-shaped members having respective bottom ends closed by bottom walls with no holes, so said phases flow through said transverse holes into each first cup-shaped member exclusively in a direction crosswise to the axes; the process being characterized by comprising the steps of: feeding the gaseous phase predominantly through first holes formed through the lateral walls of the first cup-shaped members; feeding the liquid phase predominantly through second holes also formed through the lateral walls of the first cup-shaped members and located lower down than the first holes through the lateral walls; wherein the first holes are smaller than the second holes.

The geometry of the reactor tray according to the present disclosure provides for thoroughly mixing the gaseous and liquid phases in a urea reactor and urea production process, and so greatly increasing urea output.

The reactor tray according to the present disclosure and the reactor as a whole are also extremely easy to produce and install.

Additional features and advantages are described in, and will be apparent from the following Detailed Description and the figures.

BRIEF DESCRIPTION OF THE DRAWINGS

A non-limiting embodiment of the present disclosure will be described by way of example with reference to the accompanying drawings, in which.

DETAILED DESCRIPTION

Referring now to the example embodiments of the present disclosure illustrated in FIGS. 1 to 7, FIG. 1 shows an inner portion of a urea reactor 1, in particular a tray reactor.

Reactor 1 comprises a shell 2 extending substantially along a vertical axis X and defining a reaction chamber 3 inside reactor 1; and a number or quantity of trays 4 (only one shown in FIG. 1) housed inside shell 2.

Figure 1:
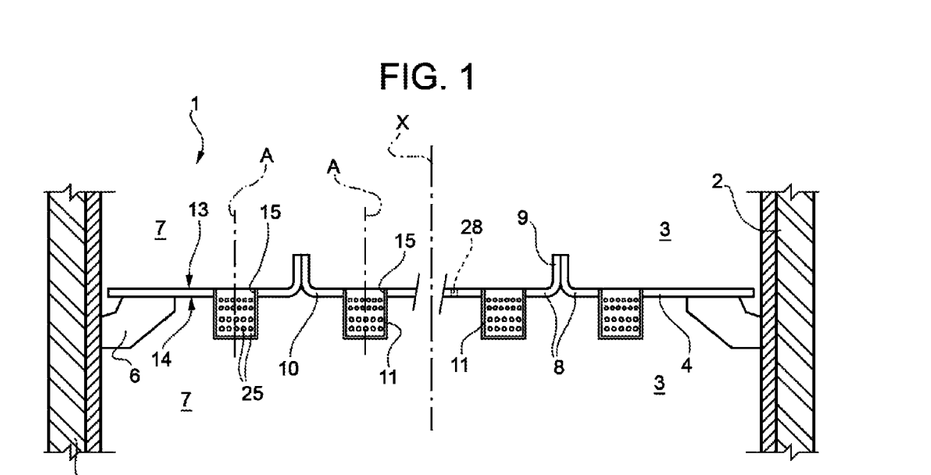
FIG. 1 shows a partial schematic of a urea reactor in accordance with a first embodiment of the disclosure.

For the sake of simplicity, other known component parts of reactor 1 not relating to the present disclosure, such as reactant and product loading and unloading systems, heating and pressurizing systems, etc., are not shown.

Shell 2 has a lateral (e.g., substantially cylindrical) wall 5; and two end portions (not shown) at respective opposite axial ends of lateral wall 5.

Trays 4 are fitted to lateral wall 5, such as by utilizing brackets 6 or other supports.

Though FIG. 1 shows only one tray 4, reactor 1 houses a number or quantity of trays 4 substantially perpendicular to and spaced along axis X to divide reaction chamber 3 into compartments 7 and define paths for the substances inside reaction chamber 3.

Each tray 4 advantageously, though not necessarily, comprises a number or quantity of removable modular sections 8 connected to one another by appropriate fastening devices 9.

Figure 2:
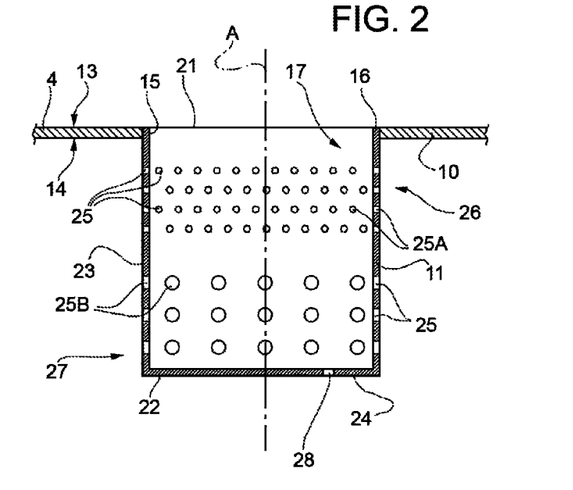
FIG. 2 shows a larger-scale detail of the FIG. 1 reactor.
Figure 3:
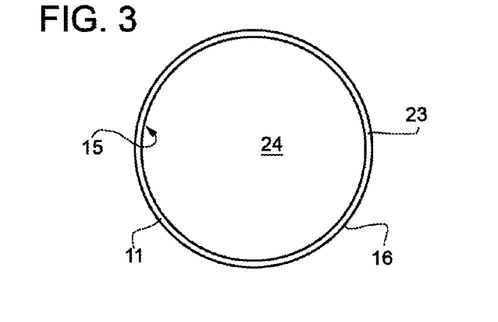
FIG. 3 shows a top plan view of the FIG. 2 detail.

With reference also to FIGS. 2 and 3, each tray 4 comprises a base plate 10 (e.g., in the form of a circular disk); and a number or quantity of cup-shaped members 11 projecting downwards from base plate 10.

More specifically, base plate 10 has a top face 13 and a bottom face 14 opposite each other and which, for example, are substantially flat and parallel.

Top face 13 has a number or quantity of openings 15 bounded by respective edges 16, such as flush with top face 13.

Cup-shaped members 11 project downwards from bottom face 14 of base plate 10.

Each cup-shaped member Ills hollow, extends vertically along an axis A substantially parallel to axis X, defines a substantially concave inner cavity 17 communicating with a respective opening 15, and extends axially between an open top end 21 with opening 15, and a closed bottom end 22.

More specifically, each cup-shaped member 11 comprises a lateral wall 23, and a bottom wall 24.

In the non-limiting example in FIGS. 1 to 3, though not necessarily, cup-shaped member 11 is substantially cylindrical: lateral wall 23 is substantially cylindrical and extends about axis A, and bottom wall 24 is substantially circular and perpendicular to axis A.

Cup-shaped members 11 may, however, be shaped differently from those described and illustrated by way of example. More specifically, they may have lateral walls 23 sloping with respect to axis A and/or other than circular cross sections (perpendicular to axis A). In other embodiments (not shown), cup-shaped members 11 may be substantially truncated-cone-shaped, prismatic, truncated-pyramid-shaped, etc. and/or have cross sections of various shapes, (e.g., substantially circular or polygonal), and either constant or varying along axis A. As opposed to being centrally symmetrical, as in the example shown, cup-shaped members 11 may even be elongated longitudinally along a horizontal axis (perpendicular to axis A). They may, for example, have a shape in plan view that is substantially rectangular or oval or basically elongated; and lateral walls 23 may be substantially parallel to axis A, or slope variously with respect to axis A to define, for example, a number or quantity of parallel or variously arranged projections beneath bottom face 14 of base plate 10.

Generally speaking, however, each cup-shaped member 11 has an open top end 21 with opening 15; and a bottom end 22 closed by bottom wall 24 with substantially no holes, as explained below.

The position of cup-shaped members 11, and more specifically of open end 21 and closed end 22, is determined by the normal flow direction of the process fluids inside reaction chamber 3. As in most reactors configured to produce urea from ammonia and carbon dioxide, the process fluids circulating in reactor 1 substantially comprise a gaseous or so-called light phase, and a liquid or so-called heavy phase. Both phases substantially flow upwards.

In the substantially axial direction (parallel to axes A and X) substantially corresponding to the flow direction of the process fluids inside reaction chamber 3, closed end 22 of each cup-shaped member 11 therefore precedes open end 21.

Regardless of its shape, lateral wall 23 has through circulation holes 25 configured to permit preferential throughflow of the liquid and/or gaseous phase.

Each cup-shaped member 11 therefore has circulation holes 25 substantially crosswise to axis A, and which, in the example shown, are substantially radial with respect to axis A.

Each cup-shaped member 11 has holes 25 of different sizes, and more specifically, has smaller holes 25A for throughflow of the gaseous (light) phase in a top area 26 close to open top end 21; and larger holes 25B for throughflow of the liquid (heavy) phase in a bottom area 27 close to closed bottom end 22.

Holes 25 may be any shape, not necessarily circular. For example, they may be circular, polygonal, oval, substantially rectangular, in the form of slots or slits, etc.

In the FIG. 2 example (which shows a more detailed view of holes 25 than in the FIG. 1 schematic), holes 25 are circular, and cup-shaped member 11 comprises a first group of holes 25A of diameter D1 in top area 26, and a second group of holes 25B of diameter D2, larger than diameter D1, in bottom area 27.

Holes 25 in both groups are, in one embodiment, equally spaced on lateral wall 23, and are arranged, for example, in a number or quantity of successive rows equally spaced axially. The holes 25 in adjacent rows may be aligned (as shown by the larger holes 25B) or staggered (as shown by the smaller holes 25A).

By way of example, the holes 25A in the first group (smaller) have a diameter D1 of roughly 2-20 mm and, in one embodiment, of about 2-4 mm; and holes 25A in the top row in the group (i.e., the row closest to open top end 21 of cup-shaped member 11 and face 14 of base plate 10) are located at a distance of roughly 1 mm or more, and, in one embodiment, of about 15-30 mm, from bottom face 14 of base plate 10.

The above measurements are purely indicative and, in the case of other than circular holes 25, may refer, as opposed to the diameter of the holes, to the equivalent or hydraulic diameter, (i.e., the diameter a circular section of the same area would have).

Holes 25A in the first group slope optionally with respect to lateral wall 23 and, more specifically, about 30° inwards and, in one embodiment, downwards with respect to the perpendicular to lateral wall 23. This slope is in no way binding, and holes 25A may even slope upwards with respect to the perpendicular to lateral wall 23. The slope of holes 25A also depends on the thickness of lateral wall 23, and serves to ensure substantially and predominantly only gaseous phase flow through holes 25A, and thorough mixing of the phases inside cup-shaped member 11.

The holes 25B in the second group (larger) have a diameter D2 of roughly 4-30 mm and, in one embodiment, of about 4-8 mm; and the row of holes 25B closest to bottom end 22 is located at a distance of 0 mm or more from bottom wall 24 to ensure throughflow of the liquid phase.

The distance from the base plate 10 of the top row of gaseous phase holes 25A (i.e., the row closes to bottom face 14 of base plate 10) is important to ensure even distribution of the gaseous phase beneath tray 4, (i.e., beneath bottom face 14 of base plate 10), by forming a uniform gaseous phase 'hood'.

In other words, in each compartment 7, both the gaseous and liquid phases of the process fluids flow upwards in a substantially axial direction (parallel to axis X), and the gaseous (light) phase accumulates against bottom face 14 of tray 4 to form a head equal in height to the distance between bottom face 14 of base plate 10 and the top row of holes 25A.

The gaseous phase therefore flows mainly through holes 25A in a substantially radial direction with respect to axes A of cup-shaped members 11, or at any rate substantially crosswise to vertical axis X of reactor 1. On reaching a sufficient head, the heavier liquid phase also flows through holes 25B, lower than holes 25A, in a direction substantially crosswise to vertical axis X of reactor 1; and both the liquid and gaseous phases flow up along cavity 17, where they are mixed locally and flow through opening 15 to the next compartment 7.

By virtue of the geometry of the present disclosure, the process fluids are therefore forced, by the compulsory paths defined by holes 25, to flow radially into each cup-shaped member 11, which therefore acts as a local mixer to ensure thorough mixing of the two phases.

Figure 4:
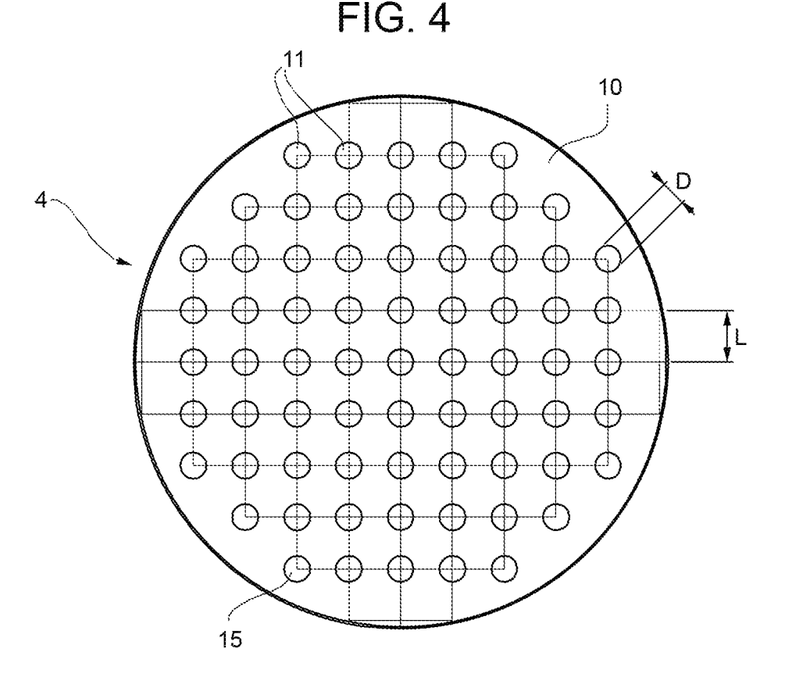
FIGS. 4 and 5 show schematic plan views of two trays usable in the FIG. 1 reactor.
Figure 5:
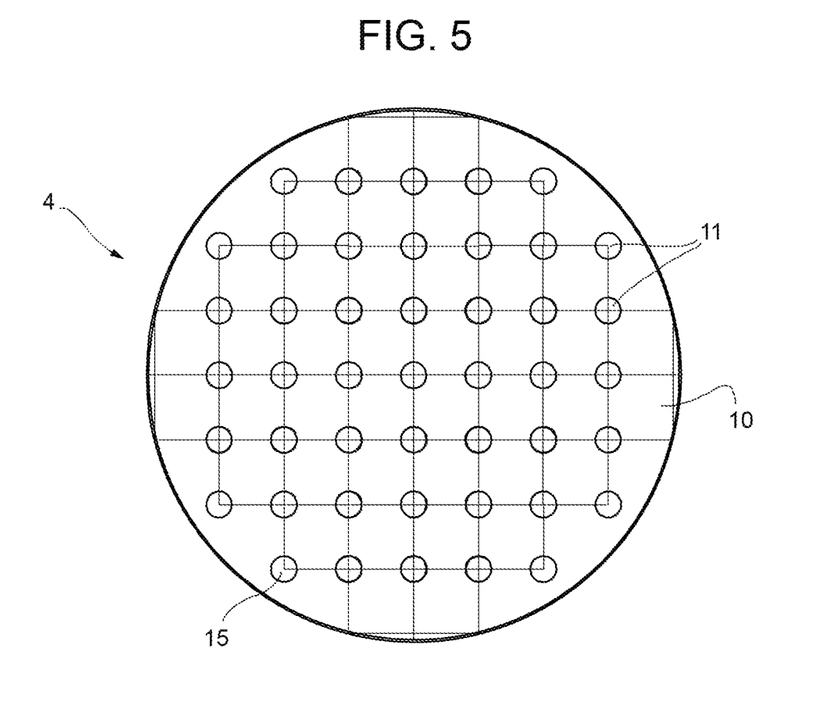

In the non-limiting examples in FIGS. 4 and 5, cup-shaped members 11 (and openings 15) are arranged on base plate 10 in a regular pattern (e.g., equally spaced in a grid pattern). More specifically, cup-shaped members 11 are spaced apart by a spacing L of roughly 1.5 D or more, such as about 2 D to 5/2 D (where D is the diameter of cup-shaped members 11) to simplify manufacture of sections 8. In other embodiments (not shown), cup-shaped members 11 are arranged on base plate 10 in other, even irregular, patterns and/or with spacings other than the one shown.

By way of example, diameter D of cup-shaped members 11 is roughly 20 mm or more, and in one embodiment about 100-160 mm.

In one embodiment, cup-shaped members 11 number fewer than 36 per square meter, and in one such embodiment, range between 12 and 18 per square meter, depending on the number or quantity of holes 25.

The number or quantity of holes 25 in the two groups (i.e., for the two phases) is selected according to the number or quantity of cup-shaped members 11 on tray 4, which in turn is selected according to the diameter and location of tray 4 inside reactor 1. Generally speaking, the geometry of tray 4 (in particular, the size and number or quantity of holes 25 and the number or quantity of cup-shaped members 11) is selected so that the total gaseous phase flow section (i.e., the total area of holes 25A) is roughly 0-20%, and, in one embodiment, about 0-4%, of the total area of tray 4, and the total liquid phase flow section (i.e., the total area of holes 25B) is roughly 1-20%, and, in one embodiment, about 1-5%, of the total area of tray 4, again depending on the location of tray 4 inside reactor 1.

Generally speaking, the total gaseous and liquid phase flow sections (i.e., the total areas of holes 25A and 25B) vary depending on the location of tray 4 inside reactor 1: trays 4 at different heights inside reactor 1 may, and in certain embodiments do, have different total gaseous and liquid phase flow sections. More specifically, working upwards from one tray 4 to the next, the total gaseous phase flow section decreases (even to practically zero at the top tray 4), while the total liquid phase flow section increases or remains substantially constant.

To avoid creating preferential paths for the two phases, there are no circulation holes (i.e., enabling direct fluid flow from one compartment 7 to another) in the surface of tray 4 (i.e., of base plate 10) or in bottom walls 24 of cup-shaped members 11.

The surface of tray 4 and/or bottom walls 24 of cup-shaped members 11 may have stagnation holes 28 to prevent the formation of stagnant gas pockets which may result in corrosion. Stagnation holes 28 (only some of which are shown schematically in FIG. 1) are smaller in diameter than both diameters D1 and D2 of gaseous and liquid phase flow holes 25, are, in one embodiment, about 2-3 mm in diameter, and are also fewer in number or quantity than holes 25, roughly by at least one order of magnitude, again to avoid creating preferential flow paths.

Bottom wall 24 therefore has substantially no holes, in the sense of having no circulation holes 25 (through which the process fluids preferably circulate), and only has optional stagnation holes 28. The term 'stagnation hole' includes a hole which, in size and/or location, does not form a preferential liquid or gaseous phase path with respect to the circulation holes.

To implement the urea production process according to the present disclosure, a reaction between ammonia and carbon dioxide is produced inside reactor 1 in appropriate pressure and temperature conditions. More specifically, the ammonia-containing liquid phase and the carbon-dioxide-containing gaseous phase are circulated upwards in the same direction inside reaction chamber 3 and through successive compartments 7 separated by trays 4.

As stated, in each compartment 7, both the liquid and gaseous phases flow upwards in a substantially axial direction (parallel to axis X) and accumulate against bottom face 14 of tray 4; the gaseous phase flows into cavities 17 of cup-shaped members 11 mainly through holes 25A, and the liquid phase into cavities 17 mainly through holes 25B; and the two phases are mixed locally inside cavities 17 and flow on to the next compartment 7.

In the FIGS. 6 and 7 embodiment, in which any details similar or identical to those already described are indicated using the same reference numbers, each tray 4 comprises base plate 10; a number or quantity of bottom first cup-shaped members 11 as described with reference to FIGS. 1 to 3, and which project vertically downwards from base plate 10 (i.e., from bottom face 14 of base plate 10); and a number or quantity of top second cup-shaped members 11A, which project upwards from base plate 10 (i.e., from top face 13 of base plate 10), and are aligned with and superimposed on respective first cup-shaped members 11.

Cup-shaped members 11A are also hollow, and extend vertically along respective axes A substantially parallel to axis X. More specifically, each cup-shaped member 11A extends, along axis A, between a closed top end 31 located over base plate 10, and an open bottom end 32 communicating with opening 15, and comprises a lateral wall 33, which extends about axis A and has through circulation holes 25C substantially crosswise to axis A and located over base plate 10; and a top end wall 34 substantially perpendicular to axis A, and which closes closed top end 31 and has substantially no holes (i.e., no circulation holes).

In other words, pairs of opposite cup-shaped members 11, 11A, superimposed vertically along axes A, project from base plate 10; and each bottom cup-shaped member 11 and the respective superimposed top cup-shaped member 11A define respective portions 35—projecting below and above base plate 10 respectively—of a tubular body 36 fitted through one of openings 15 in base plate 10.

Each cup-shaped member 11A has a substantially concave inner cavity 37, which communicates with opening 15 and with one cavity 17 of cup-shaped member 11 underneath.

Holes 25C in lateral wall 33 of each top cup-shaped member 11A are, for example, similar or identical in shape and arrangement to the predominantly liquid phase circulation holes 25B of respective bottom cup-shaped member 11. More specifically, holes 25C of each top cup-shaped member 11A have a total area (defining the total flow section for both phases through cup-shaped member 11A) substantially equal to the total area of holes 25B of the corresponding bottom cup-shaped member 11.

For example, the size of holes 25C and the number or quantity of holes 25C and cup-shaped members 11A are selected so that the total flow section for both phases (i.e., the total area of holes 25C) is roughly 1-20%, and, in one embodiment, about 1-5%, of the total area of tray 4, depending on the location of tray 4 inside reactor 1.

In this variation, too, a reaction between ammonia and carbon dioxide is produced inside reactor 1 in appropriate pressure and temperature conditions. More specifically, the ammonia-containing liquid phase and the carbon-dioxide-containing gaseous phase are circulated upwards in the same direction inside reaction chamber 3 and through successive compartments 7 separated by trays 4.

As stated, in each compartment 7, both the liquid and gaseous phases flow upwards in a substantially axial direction (parallel to axis X) and accumulate against bottom face 14 of tray 4; the gaseous phase flows into cavities 17 of cup-shaped members 11 mainly through holes 25A, and the liquid phase into cavities 17 mainly through holes 25B; and the two phases are mixed locally inside cavities 17.

Both phases flow upwards in a substantially axial (vertical) direction inside cup-shaped members 11, and into cup-shaped members 11A aligned with and superimposed on respective cup-shaped members 11, and flow out of cup-shaped members 11A through holes 25C (i.e., exclusively crosswise to axes A), and on to the next compartment 7.

In this variation, too, there are no circulation holes (i.e., enabling direct flow from one compartment 7 to another), in the surface of tray 4 (i.e., of base plate 10) or in end walls 24, 34 of cup-shaped members 11, 11A, to avoid creating preferential paths for the gaseous and/or liquid phase.

The surface of tray 4 and/or bottom walls 24 and/or end walls 34 have optional stagnation holes 28 as described above.

Figure 6:
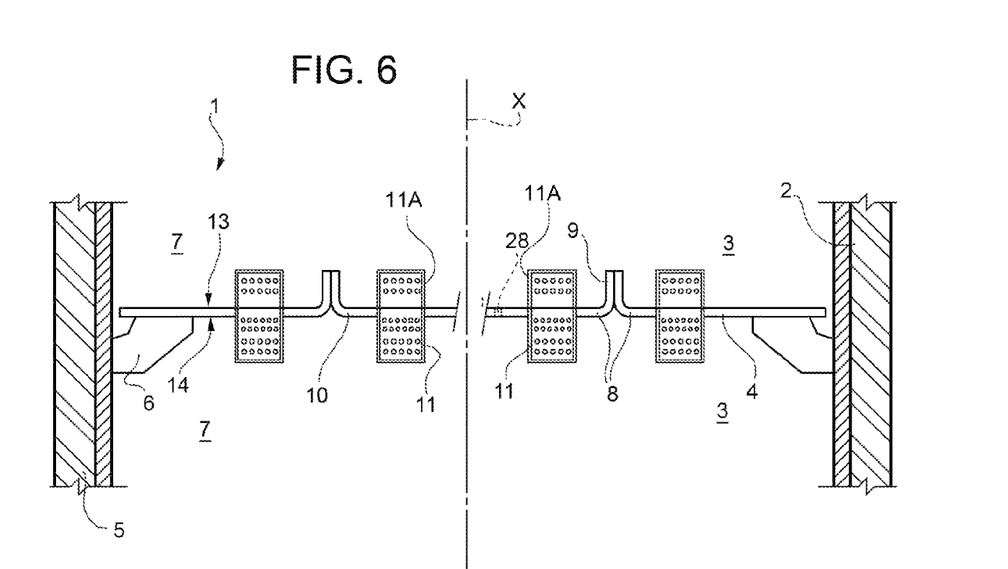
FIG. 6 shows a partial schematic of a urea reactor in accordance with a second embodiment of the disclosure.
Figure 7:
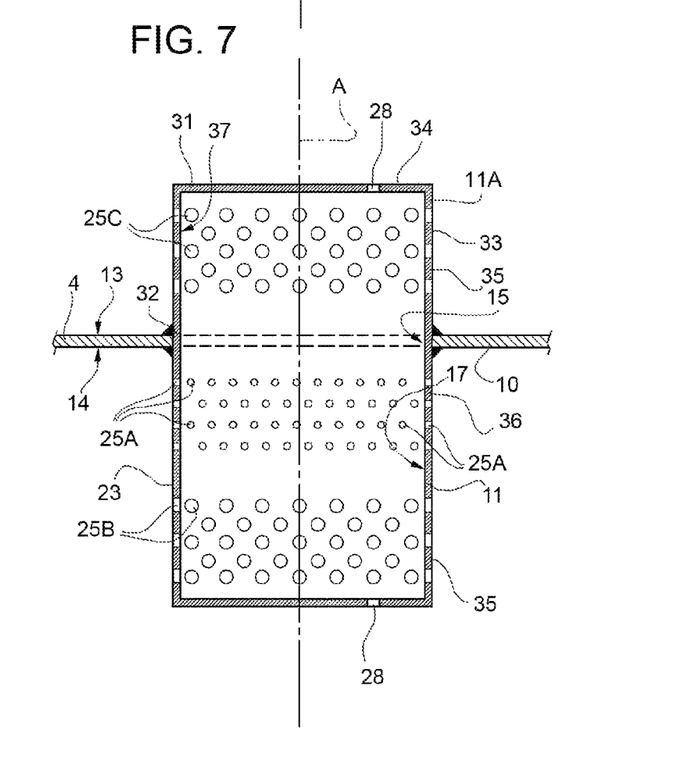
FIG. 7 shows a larger-scale detail of the FIG. 6 reactor.

The additional characteristics referred to above with reference to FIGS. 1-5, and relating, for example, to the size and arrangement of the circulation holes and cup-shaped members, also apply to the FIGS. 6 and 7 variation.

Clearly, changes may be made to the reactor tray, reactor, and process as described and illustrated herein without, however, departing from the scope of the accompanying Claims. That is, various changes and modifications to the presently disclosed embodiments will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A urea reactor tray comprising:
   a base plate;
   a first cup-shaped member which projects in a downward direction from a bottom face of the base plate along an axis transverse to the base plate, and which defines a substantially concave inner cavity communicating with an opening defined by the base plate, and which extends axially between an open top end defined by the opening defined by the base plate and a closed bottom end, said first cup-shaped member including:
      a lateral wall which defines a plurality of through circulation holes substantially crosswise to the axis of said first cup-shaped member, said circulation holes including a plurality of first circulation holes predominantly configured for throughflow of a gaseous phase, and a plurality of second circulation holes predominantly configured for throughflow of a liquid phase, the plurality of first circulation holes being located closer to the open top end of the first cup-shaped member than the plurality of second circulation holes, and the plurality of first circulation holes being smaller than the plurality of second circulation holes; and a bottom wall attached to the lateral wall and which does not define any circulation holes; and a second cup-shaped member aligned with and superimposed on the first cup-shaped member, said second cup-shaped member projecting in an upward direction from the base late between the closed to end over the base late and the open bottom end communicating with the opening defined by the base plate, the second cup-shaped member including:

a lateral wall which defines a plurality of third through circulation holes substantially crosswise to the axis of said superimposed first cup-shaped member and located over the base plate, and a top end wall which closes the closed top end, is transverse to the axis of the superimposed first cup-shaped member, and does not define any circulation holes.

2. The urea reactor tray of claim 1, wherein the plurality of first circulation holes are located in a top area of the first cup-shaped member and close to the open top end of the first cup-shaped member, and the plurality of second circulation holes are located in a bottom area of the first cup-shaped member and close to the closed bottom end of the first cup-shaped member.

3. The urea reactor tray of claim 1, wherein the plurality of first circulation holes of the first cup-shaped member each have a diameter of approximately 2 mm to 20 mm and the plurality of second circulation holes of the first cup-shaped member each have a diameter of approximately 4 mm to 30 mm.

4. The urea reactor tray of claim 3, wherein the plurality of first circulation holes of the first cup-shaped member each have the diameter of approximately 2 mm to 4 mm and the plurality of second circulation holes of the first cup-shaped member each have the diameter of approximately 4 mm to 8 mm.

5. The urea reactor tray of claim 1, wherein the plurality of first circulation holes of the first cup-shaped member are arranged in at least one of a plurality of axially successive rows and the row closest to the open top end of the first cup-shaped member is approximately located at a distance of at least mm from the bottom face of the base plate.

6. The urea reactor tray of claim 5, wherein the row closest to the open top end of the first cup-shaped member is located at a distance of approximately 15 mm to 20 mm from the bottom face of the base plate.

7. The urea reactor tray of claim 1, wherein the plurality of first circulation holes of the first cup-shaped member slope with respect to the lateral wall of the first cup-shaped member.

8. The urea reactor tray of claim 1, wherein the plurality of second circulation holes of the first cup-shaped member are arranged in at least one of a plurality of axially successive rows and the row closest to the closed bottom end of the first cup-shaped member is approximately located at a distance of at least 0 mm from the bottom wall of the first cup-shaped member.

9. The urea reactor tray of claim 1, wherein a size of the plurality of first circulation holes, a size of the plurality of second circulation holes, and the first cup-shaped member are such that a total area of the plurality of first circulation holes ranges between approximately 0% and 20% of a total area of the urea reactor tray, and a total area of the plurality of second circulation holes ranges between approximately 1% and 20% of the total area of the urea reactor tray.

10. The urea reactor tray of claim 9, wherein the total area of the plurality of first circulation holes ranges between approximately 0% and 4% of the total area of the urea reactor tray, and the total area of the plurality of second circulation holes ranges between approximately 1% and 5% of the total area of the urea reactor tray.

11. The urea reactor tray of claim 1, wherein the first cup-shaped member and the superimposed second cup-shaped member define a plurality of respective portions of a tubular body fitted through the opening defined by the base plate, said portions projecting beneath the base plate and above the base plate.

12. The urea reactor tray of claim 1, wherein the third circulation holes of the lateral wall of the second cup-shaped member are based on a shape and arrangement of the plurality of second circulation holes of the superimposed first cup-shaped member and said third circulation holes are predominantly configured for throughflow of the liquid phase.

13. The urea reactor tray of claim 1, wherein the first cup-shaped member and the second cup-shaped member are arranged on the base plate in a grid pattern with a spacing ranging between approximately 2D and 5/2D, wherein D is a diameter of at least one of: the first cup-shaped member and the second cup-shaped member.

14. The urea reactor tray of claim 1, which includes a plurality of first cup-shaped members and a plurality of second cup-shaped members.

15. The urea reactor tray of claim 1, wherein the cup-shaped member is substantially cylindrical.

16. The urea reactor tray of claim 1, which includes a plurality of base plates.

17. The urea reactor tray of claim 1, which includes a plurality of first cup-shaped members.

18. The urea reactor tray of claim 1, wherein the first cup-shaped member is hollow.

19. A urea reactor comprising:
a shell extending substantially along a first axis and defining a reaction chamber; and
a reactor tray inside the shell, said reactor tray separating the reaction chamber into a plurality of compartments, and said reactor tray including:
a base plate; and
a first cup-shaped member which projects in a downward direction from a bottom face of the base plate along an axis transverse to the base plate, and which defines a substantially concave inner cavity communicating with an opening defined by the base plate, and which extends axially between an open top end defined by the opening defined by the base plate and a closed bottom end, said first cup-shaped member including:
a lateral wall which defines a plurality of through circulation holes substantially crosswise to the axis of said first cup-shaped member, said circulation holes including a plurality of first circulation holes predominantly configured for throughflow of a carbon-dioxide containing gaseous phase, and a plurality of second circulation holes predominantly configured for throughflow of an ammonia containing liquid phase, the plurality of first circulation holes being located closer to the open top end of the first cup-shaped member than the plurality of second circulation holes, and the plurality of first circulation holes being smaller than the plurality of second circulation holes; and a bottom wall attached to the lateral wall and which does not define any circulation holes which permit direct fluid flow from one compartment to another compartment, wherein:

(i) both the ammonia containing liquid phase and the carbon-dioxide containing gaseous phase cocurrently flow in an upward direction aligned with the axis transverse to the base plate to accumulate against said bottom face of the base plate of the reactor tray, (ii) after the carbon-dioxide containing gaseous phase forms a designated head defined by a distance between the bottom face of the base plate of the reactor tray and a top row of first circulation holes, both the ammonia containing liquid phase and the carbon-dioxide containing gaseous phase enter radially into the first cup-shaped member, and (iii) both the ammonia containing liquid phase and the carbon-dioxide containing gaseous phase cocurrently flow in the upward direction aligned with the axis transverse to the base plate to exit from the first cup-shaped member.

20. The urea reactor of claim 19, wherein the reactor tray is positioned with the base plate substantially transverse to the first axis such that, in an upward direction substantially corresponding to a flow direction inside the reaction chamber, the first cup-shaped member projects in the downward direction from the base plate with the closed bottom end of the first cup-shaped member preceding the open top end of the first cup-shaped member.

21. The urea reactor of claim 19, which includes a plurality of reactor trays at different heights along the first axis having respective first circulation holes and second circulation holes whose total areas, which define respective total flow sections for the gaseous phase and liquid phase, differ according to a location of the reactor tray inside the reactor and a total area of the first circulation holes decreases in an upward direction from one reactor tray to another reactor tray, and a total area of the second circulation holes increases in the upward direction from one reactor tray to another reactor tray.

22. A urea reactor comprising:

a shell extending substantially along a first axis and defining a reaction chamber; and a plurality of reactor trays housed in a mutual spatial relationship inside the shell, each reactor tray including:

a base plate;

a first cup-shaped member which projects in a downward direction from a bottom face of the base plate along an axis transverse to the base plate, and which defines a substantially concave inner cavity communicating with an opening defined by the base plate, and which extends axially between an open top end defined by the opening defined by the base plate and a closed bottom end, said first cup-shaped member including:

a lateral wall which defines a plurality of through circulation holes substantially crosswise to the axis of said first cup-shaped member, said circulation holes including a plurality of first circulation holes predominantly configured for throughflow of a gaseous phase, and a plurality of second circulation holes predominantly configured for throughflow of a liquid phase, the plurality of first circulation holes being located closer to the open top end of the first cup-shaped member than the plurality of second circulation holes, and the plurality of first circulation holes being smaller than the plurality of second circulation holes; and a bottom wall attached to the lateral wall and which does not define any circulation holes; and a second cup-shaped member aligned with and superimposed on the first cup-shaped member, said second cup-shaped member projecting in an upward direction from the base plate between the closed top end over the base plate and the open bottom end communicating with the opening defined by the base plate, the second cup-shaped member including:

a lateral wall which defines a plurality of third through circulation holes substantially crosswise to the axis of said superimposed first cup-shaped member and located over the base plate, and a top end wall which closes the closed top end, is transverse to the axis of the superimposed first cup-shaped member, and does not define any circulation holes.

23. The urea reactor of claim 22, wherein each reactor tray is positioned with the base plate substantially transverse to the first axis such that, in an upward direction substantially corresponding to a flow direction inside the reaction chamber, the first cup-shaped member projects in the downward direction from the base plate with the closed bottom end of the first cup-shaped member preceding the open top end of the first cup-shaped member.

24. The urea reactor of claim 22, wherein reactor trays at different heights along the first axis have respective first circulation holes and second circulation holes whose total areas, which define respective total flow sections for the gaseous phase and liquid phase, differ according to a location of the reactor tray inside the reactor and a total area of the first circulation holes decreases in an upward direction from one reactor tray to another reactor tray, and a total area of the second circulation holes increases in the upward direction from one reactor tray to another reactor tray.

25. The urea reactor of claim 22, wherein the first cup-shaped member and the superimposed second cup-shaped member define a plurality of respective portions of a tubular body fitted through the opening defined by the base plate, said portions projecting beneath the base plate and above the base plate.

26. The urea reactor of claim 22, wherein the third circulation holes of the lateral wall of the second cup-shaped member are based on a shape and arrangement of the plurality of second circulation holes of the superimposed first cup-shaped member and said third circulation holes are predominantly configured for throughflow of the liquid phase.

27. The urea reactor of claim 22, wherein the first cup-shaped member and the second cup-shaped member are arranged on the base plate in a grid pattern with a spacing ranging between approximately 2D and 5/2D, wherein D is a diameter of at least one of: the first cup-shaped member and the second cup-shaped member.

28. The urea reactor of claim 22, which includes a plurality of first cup-shaped members and a plurality of second cup-shaped members.

* * * * *